(12) United States Patent
Lichten

(10) Patent No.: US 10,248,761 B2
(45) Date of Patent: Apr. 2, 2019

(54) COMPUTERIZED SYSTEM AND METHOD FOR RECORDING AND TRACKING DERMATOLOGICAL LESIONS

(71) Applicant: Mole MapperPlus, LLC, Akron, OH (US)

(72) Inventor: Gary Lichten, Akron, OH (US)

(73) Assignee: Derm Mapper, LLC, Akron, OH (US)

( * ) Notice: Subject to any disclaimer, the term of this patent is extended or adjusted under 35 U.S.C. 154(b) by 557 days.

(21) Appl. No.: 14/983,676

(22) Filed: Dec. 30, 2015

(65) Prior Publication Data
US 2016/0196385 A1 Jul. 7, 2016

Related U.S. Application Data

(60) Provisional application No. 62/117,495, filed on Feb. 18, 2015, provisional application No. 62/100,896, filed on Jan. 7, 2015.

(51) Int. Cl.
A61B 5/00 (2006.01)
G06F 19/00 (2018.01)
H04N 5/232 (2006.01)
G16H 10/60 (2018.01)

(52) U.S. Cl.
CPC .......... G06F 19/321 (2013.01); A61B 5/0077 (2013.01); A61B 5/444 (2013.01); G16H 10/60 (2018.01); H04N 5/23222 (2013.01); H04N 5/23293 (2013.01); A61B 5/7425 (2013.01)

(58) Field of Classification Search
CPC combination set(s) only.
See application file for complete search history.

(56) References Cited

U.S. PATENT DOCUMENTS

| | | | | |
|---|---|---|---|---|
| 5,016,173 A * | 5/1991 | Kenet | ................... | A61B 5/0059 382/128 |
| 5,531,520 A * | 7/1996 | Grimson | ................ | G01B 11/25 382/131 |
| 5,774,172 A | 6/1998 | Kappell | | |
| 5,999,840 A * | 12/1999 | Grimson | ................ | G06T 3/0068 600/424 |
| 6,628,983 B1 * | 9/2003 | Gagnon | ................ | G01T 1/1648 600/431 |
| 6,993,167 B1 * | 1/2006 | Skladnev | .............. | A61B 5/0059 382/128 |
| 8,109,875 B2 | 2/2012 | Gizewski | | |

(Continued)

Primary Examiner — Tsung Yin Tsai
(74) Attorney, Agent, or Firm — Kevin Keener; Keener and Associates P.C.

(57) ABSTRACT

A computerized method for recording and tracking dermatological lesions is disclosed. The method comprises creating a graphical template of a portion of a human form to assist in taking a photograph of the human body. A composite image of the template and video input are displayed to ensure accuracy of the image. The system also permits a user to highlight multiple dermatological lesions present on the body. When a user highlights the location of a lesion the system prompts the user to create an enhanced zoom image to capture details of the lesion. When multiple enhanced zoom images are created the system permits a user to create a merged image of multiple images of the lesion. The system aligns the images and creates visual accents to quickly display the differences between the photographs, allowing a user to quickly identify changes in the lesion over time.

20 Claims, 21 Drawing Sheets

(56) References Cited

U.S. PATENT DOCUMENTS

| | | |
|---|---|---|
| 8,275,449 B2 | 9/2012 | White et al. |
| 8,600,134 B2 | 12/2013 | Vercauteren et al. |
| 8,755,053 B2 * | 6/2014 | Fright .................. A61B 5/1077 356/604 |
| 8,782,713 B2 | 7/2014 | Kalva et al. |
| 8,830,356 B2 | 9/2014 | Balannik et al. |
| 8,891,841 B2 | 11/2014 | Schultz et al. |
| 2002/0141626 A1 * | 10/2002 | Caspi .................... G06T 3/0068 382/131 |
| 2006/0005168 A1 | 1/2006 | Singh |
| 2012/0173278 A1 | 7/2012 | Herbst et al. |
| 2013/0212510 A1 | 8/2013 | Choi et al. |
| 2013/0298082 A1 | 11/2013 | Soffer et al. |
| 2014/0088440 A1 | 3/2014 | Swart et al. |
| 2014/0161342 A1 | 6/2014 | Schauer et al. |
| 2014/0164968 A1 | 6/2014 | Aalami |
| 2014/0164970 A1 | 6/2014 | Felt |
| 2014/0313303 A1 * | 10/2014 | Davis ....................... A61B 5/68 348/77 |
| 2014/0378810 A1 * | 12/2014 | Davis ........................ G06T 5/40 600/407 |
| 2016/0183879 A1 * | 6/2016 | Goldish ................. A61B 5/702 600/474 |

* cited by examiner

COMPUTERIZED SYSTEM AND METHOD FOR RECORDING AND TRACKING DERMATOLOGICAL LESIONS

PRIORITY

This application claims priority to U.S. Provisional Patent Ser. No. 62/100,896 filed Jan. 7, 2015 and U.S. Provisional Patent Ser. No. 62/117,495 filed Feb. 18, 2015.

FIELD OF THE INVENTION

The invention pertains generally to a software system to be utilized for medical purposes and more particularly to a system and method for recording, tracking, and monitoring a patient's epidermis for the existence of skin lesions and changes in skin lesions.

BACKGROUND OF INVENTION

Skin related diseases exhibit a large toll on public health. Skin cancers can be ravaging on individuals, requiring chemotherapy, radiation, and/or surgery. Survival of skin cancer is best when an individual detects the existence of the lesion early and can start treatment as early as possible. For this reason, doctors suggest yearly screening visits to dermatologists. During these visits dermatologists often use optical medical devices such as dermatoscopes to view moles and possible lesions for characteristics which could be attributed to skin cancer. If a dermatologist detects a lesion with characteristics indicative of skin cancer then the dermatologist can take remedial actions, such as removing the lesion for further testing.

One characteristic which dermatologists will take note of as a possibility of skin cancer is any change in the shape, size, or color of a lesion over time. For instance, if a patient has a mole which gets larger over the course of a year, a dermatologist is likely to take note and flag the mole for further review or remedial action. Tools have been developed to assist dermatologists in tracking skin lesions over time. Dermatologists may take digital photos of moles and possible lesions to store on a computer system. A dermatologist may take an initial photo of a possible lesion or a mole to operate as a base line for later comparison. At a later visit from the patient, the dermatologist can take additional digital photos of the same mole or possible lesion to compare against the base line photos. If a dermatologist sees changes when comparing the photos the dermatologist can then take follow up action with respect to that specific mole or lesion.

Some systems permit a dermatologist to take photos of moles and possible lesions, and track changes in those moles and possible lesions. However, current systems are limited in that they are physician-centric. They are developed for use solely by dermatologists. These systems are limited in that patients are required to travel to a doctor's office for the systems to be used. The systems do not solve the problems faced when patients fail to travel to the doctor's office or fail to keep a yearly appointment. What is needed is a system and method guiding patients to remotely self-photograph themselves for storage, transmission, and review by the patient's physician. Furthermore, systems are needed which provide templates as guides for individuals to take proper photographs of themselves for later analysis and systems which assists in analysis by allowing a user to directly compare multiple images of lesions to detect change.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The invention is directed toward a computerized method for tracking and analyzing skin lesions comprising displaying a graphical template image consisting of a portion of a human form on a display screen of a computerized device, receiving a video input from a camera, displaying the video input on the display screen, creating a composite image consisting of the graphical template image and the video input, displaying the composite image on the display screen, receiving an instruction to capture a photographic image from the video input, creating and storing a first photographic image from the video input, receiving a selection of a portion of the first photographic image containing a dermatological lesion, highlighting the selection on the first photographic image on the display, creating a prompt to create a second photographic zoomed image of the dermatological lesion in response to receiving a selection of a portion of the first photographic image, receiving an instruction to capture a second photographic image from the video input, and creating and storing a second photographic image from the video input.

In another embodiment of the invention, the method further comprises creating and storing a third photographic zoomed image of the dermatological lesion from the video input, displaying the second photographic image and the third photographic image adjacent on the display screen, receiving an instruction to display a merged image of the second photographic image and the third photographic image, creating a merged image of the second photographic image and the third photographic image, aligning one or more topographical features of the dermatological lesion in the second photographic image with one or more topographical features of the dermatological lesion in the third photographic image, and accenting one or more differences in one or more topographical features between the dermatological lesion in the second photographic image and the dermatological lesion in the third photographic image to provide a physician with information to make a diagnostic determination with respect to the dermatological lesion.

In another embodiment of the invention, the method further comprises creating a red circle surrounding a selection on the first photographic image on the display. The method may further comprise receiving a video input from a dermatoscope communicatively coupled to the computerized device. The method may further comprise adjusting the transparency the second photographic image when creating the merged image, adjusting the transparency of the third photographic image when creating the merged image, or adjusting the transparency of both when creating the merged image. The method may further comprise adjusting the transparency of the video input when creating the composite image or adjusting the transparency of the graphical template image when creating the composite image.

In another embodiment of the invention, the method further comprises requesting input regarding diagnostic information, one or more characteristics, one or more symptoms, and one or more action items of one or more dermatological lesions. The method may further comprise receiving input regarding diagnostic information, one or more characteristics, one or more symptoms, and one or more action items of one or more dermatological lesions. The method may further comprise storing input regarding diagnostic information, one or more characteristics, one or more symptoms, and one or more action items of one or more dermatological lesions. The method may further comprise linking input regarding diagnostic information, one or more characteristics, one or more symptoms, and one or more action items of one or more dermatological lesions with a respective photographic image of a dermatological lesion. The method may further comprise displaying input regarding diagnostic information, one or more characteristics, one or more symptoms, and one or more action items of one or more dermatological lesions adjacent to a respectively linked photographic image of a dermatological lesion.

In another embodiment of the invention, the method further comprises displaying an internal organ graphical template image consisting of a portion of a human internal organ on a display screen of a computerized device, receiving a video input from an internal imaging device coupled to the computerized device, displaying the video input from the internal imaging device on the display screen, creating an internal composite image consisting of the internal organ graphical template image and the video input from the internal imaging device, displaying the internal composite image on the display screen, receiving an instruction to capture a photographic image from the video input from the internal imaging device, and creating and storing a first photographic image from the video input from the internal imaging device.

In another embodiment of the invention, the method further comprises creating a first test result image from a medical device input, creating a second test result image from a medical device input, displaying the first test result image and the second test result image adjacent on the display screen, receiving an instruction to display a merged test result image of the first test result image and the second test result image. creating a merged image of the first test result image and the second test result image, aligning one or more features of the first test result image with one or more features of the second test result image, and accenting one or more differences in one or more features between the first test result image and the second test result image to provide a physician with information to make a diagnostic determination with respect to the dermatological lesion.

In another embodiment of the invention, the method further comprises receiving an instruction to create a password protected user ID, creating a password protected user ID, linking one or more photographic images to the password protected user ID, receiving a request for access to one or more photographic images linked to the password protected user ID, verifying the authenticity of a password associated with the password protected user ID, and displaying one or more photographic images on the display screen when the password is authenticated.

In another embodiment of the invention, the method further comprises receiving a photographic image of a portion of a medical chart on the computerized device, creating and storing a digital copy of the medical chart on the computerized device, and displaying the digital copy of the medical chart on the display screen.

Still other embodiments of the present invention will become readily apparent to those skilled in this art from the following description wherein there is shown and described the embodiments of this invention, simply by way of illustration of the best modes suited to carry out the invention. As it will be realized, the invention is capable of other different embodiments and its several details are capable of modifications in various obvious aspects all without departing from the scope of the invention. Accordingly, the drawing and descriptions will be regarded as illustrative in nature and not as restrictive.

BRIEF DESCRIPTION OF THE DRAWINGS

Various exemplary embodiments of this invention will be described in detail, wherein like reference numerals refer to identical or similar components, with reference to the following figures, wherein.

DETAILED DESCRIPTION OF THE PREFERRED EMBODIMENT

The claimed subject matter is now described with reference to the drawings. In the following description, for purposes of explanation, numerous specific details are set forth in order to provide a thorough understanding of the claimed subject matter. It may be evident, however, that the claimed subject matter may be practiced with or without any combination of these specific details, without departing from the spirit and scope of this invention and the claims.

As used in this application, the terms "component", "module", "system", "interface", or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component.

In the following description, for purposes of explanation, numerous specific details are set forth in order to provide a thorough understanding of the claimed subject matter. It may be evident, however, that the claimed subject matter may be practiced with or without any combination of these specific details, without departing from the spirit and scope of this invention and the claims.

The invention is directed toward a computerized method and system for photographing, tracking, reviewing, and comparing moles and skin lesions exhibited by a patient. The skin lesions photographed, tracked, reviewed, and compared may be any type of skin lesion or skin condition, including but not limited to immunological skin conditions, infectious skin conditions, allergic skin conditions, neoplastic skin conditions, drug induced skin conditions, genetic skin conditions, and inflammatory skin conditions.

Figure 1:
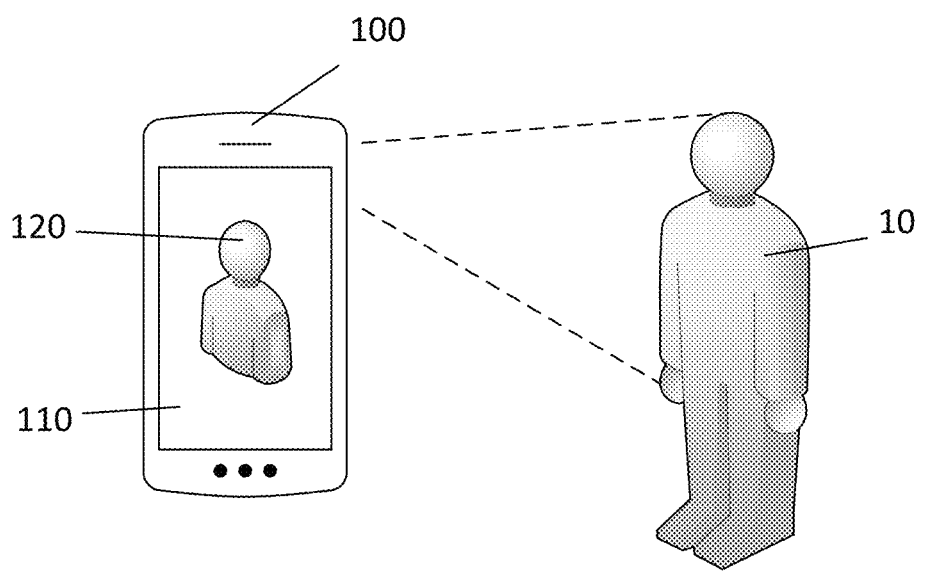
FIG. 1 is an illustration of the system utilized on a patient.
Figure 2:
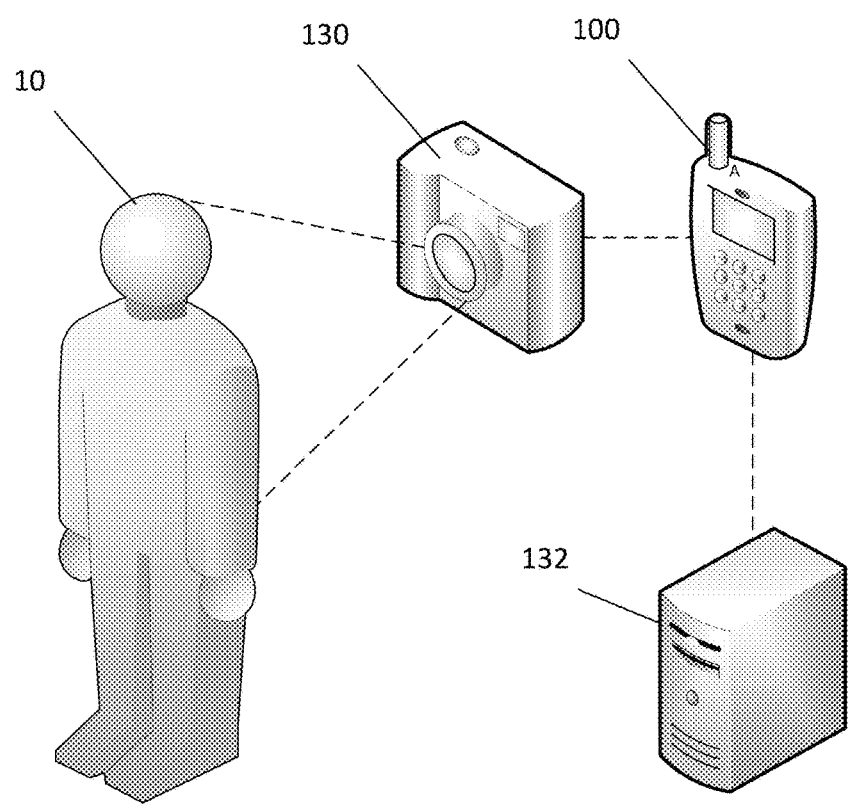
FIG. 2 is an illustration of the system utilized on a patient.

The system is illustrated in FIG. 1 and FIG. 2. The system comprises one or more client devices 100 and a server computer 132. The client device 100 may be any type of computerized device capable of executing instructions stored on the client device 100. The client device 100 may be a laptop computer, desktop computer, tablet computer, or wireless cellular device. In the preferred embodiment the client device 100 has a camera incorporated into the device and a display screen 110 for displaying the images recorded by the camera. In other embodiments the system further comprises a separate camera device 130, such as a dermatoscope. In this embodiment the dermatoscope 130 may be attached to the client device 100 for the purposes of taking photographs of the patient. The server computer 132 is communicatively coupled to a plurality of client devices 100. The server computer 132 may be directly linked to the client devices 100 or communicatively coupled through a network connection, like the internet. The system may have one or more software modules stored on the server computer 132 and client device 100. The software may be fully executed on the server computer 132 while the patient 10 interacts with the software module from the client device 100 through a network connection. Alternatively, certain software modules may be stored and executed on the server computer 132 while other software modules are stored and executed on the client device 100. In the preferred embodiment, each patient 10 utilizing the system creates a unique user ID and password for accessing information. Additionally, in the preferred embodiment, the patient 10 links the patient's account with the patient's physician so that both the patient 10 and the physician may access the patient's account.

In other embodiments of the system, the server computer 132 and client computers 100 are not interconnected over the internet for the purposes of protected patient information. In this embodiment, the patients 10 may take photographs in the privacy of their own home on their personal client device 100. The patient 10 then brings the client device 100 with them at the time of their next physician's visit. The patient 10 can then directly port photographs and information from the client device 100 to the server computer 132. Optionally, the patient 10 may transfer information from the client device 100 to a portable zip drive. The patient 10 may then transfer the information from the zip drive to the server computer 132 at the time of visiting the physician.

The invention utilizes a unique system and computerized method to track changes to skin lesions and moles. The system begins when a patient 10 creates the patient's account and links the patient's account with the patient's physician. The patient 10 then prepares to take base line photographs of the patient's skin. The patient 10 points the camera at the patient's skin and takes pictures of portions of the patient's skin.

Figure 3:
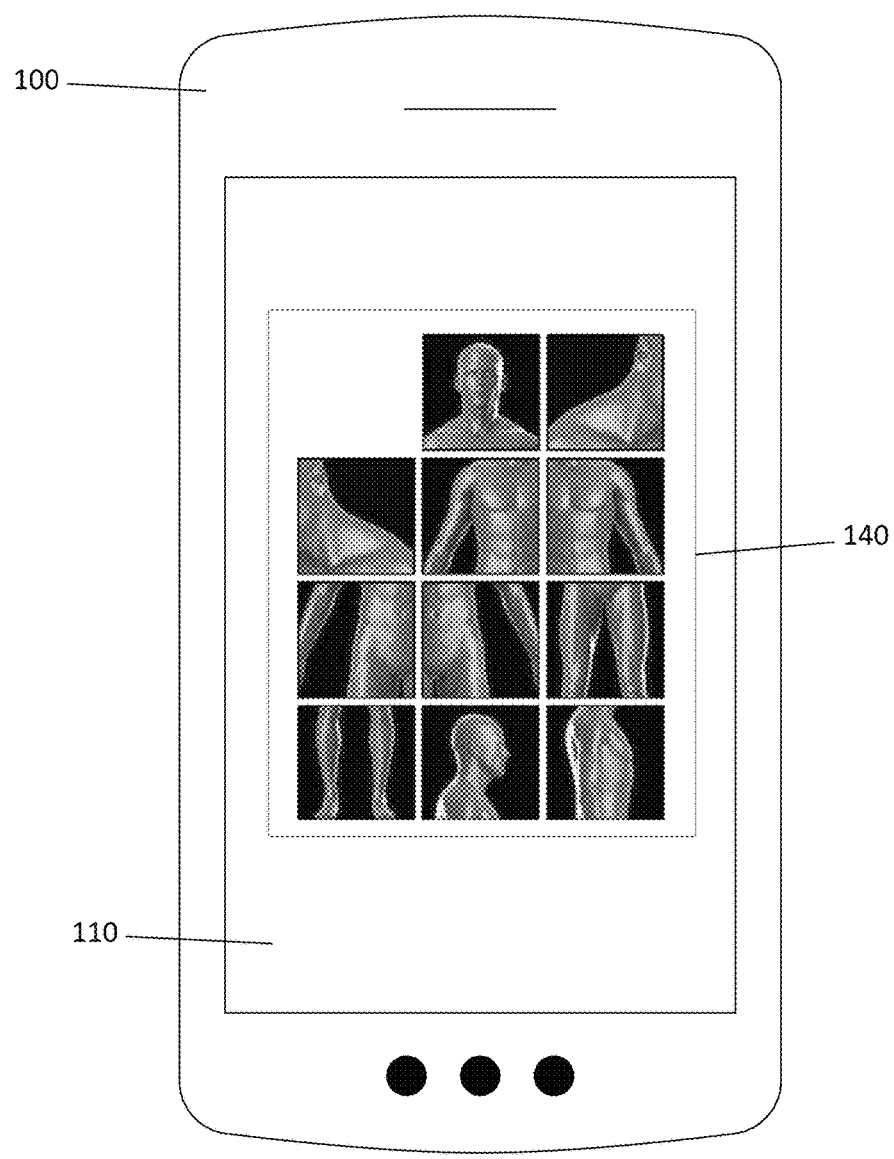
FIG. 3 is an illustration of the display of a computerized device utilizing the invention.
Figure 4:
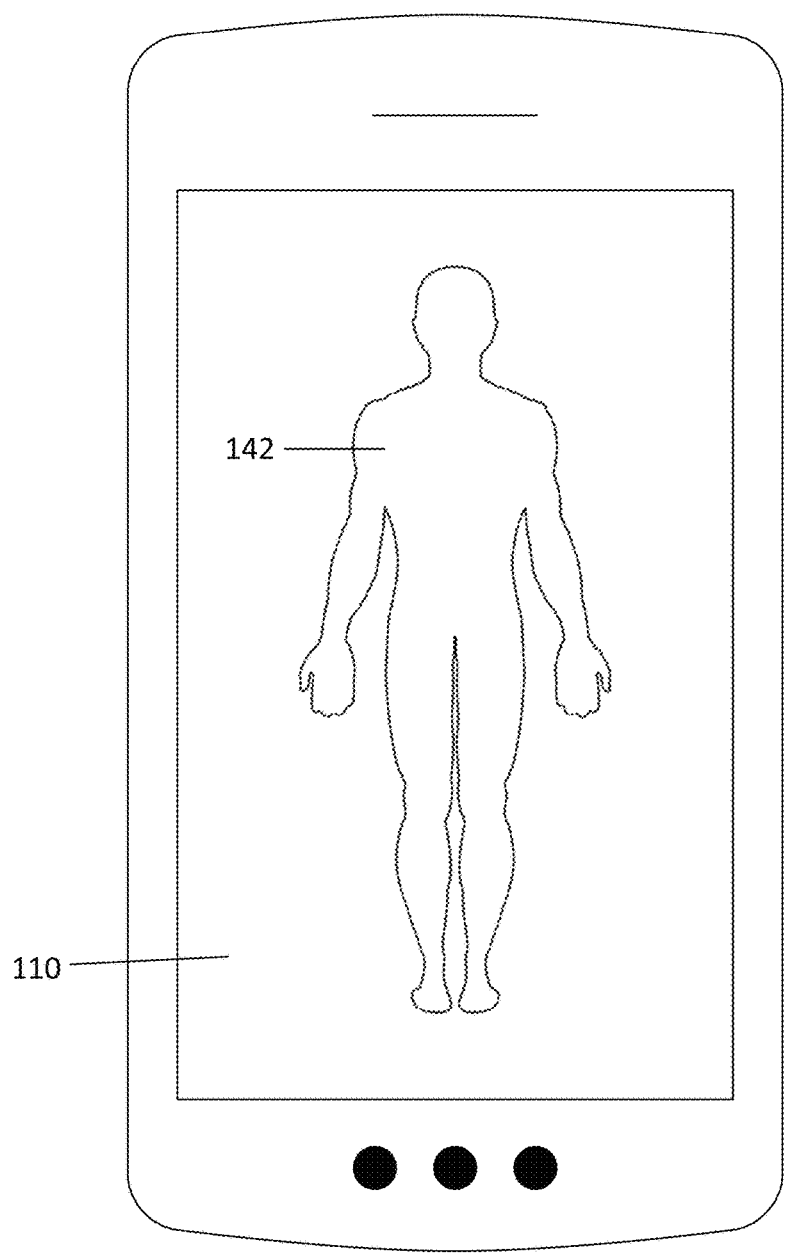
FIG. 4 is an illustration of the display of a computerized device utilizing the invention.

As shown in FIG. 3, the system first presents an array 140 of body templates to the patient for taking photographs of the patient's skin. The array 140 of body templates displays a series of portions of human form to guide the patient 10 in taking proper photographs of the patient's skin. Each photograph taken by the user is stored on the client device 100 in association with the appropriate template. Referring to FIG. 4, the display screen 110 of the client device 100 displays a transparent guidance template 142. The transparent guidance template 142 displays a specific section of a human form. For instance, the guidance template 142 may present an image of the entire human body or a portion of the human body, such as strictly a head, a hand, a foot, a leg, a torso, or any portion thereof. In addition, the guidance template 142 may present a portion of a human form from one or more directions, such as the front of a leg, the back of a leg, or the side of a leg.

Figure 5:
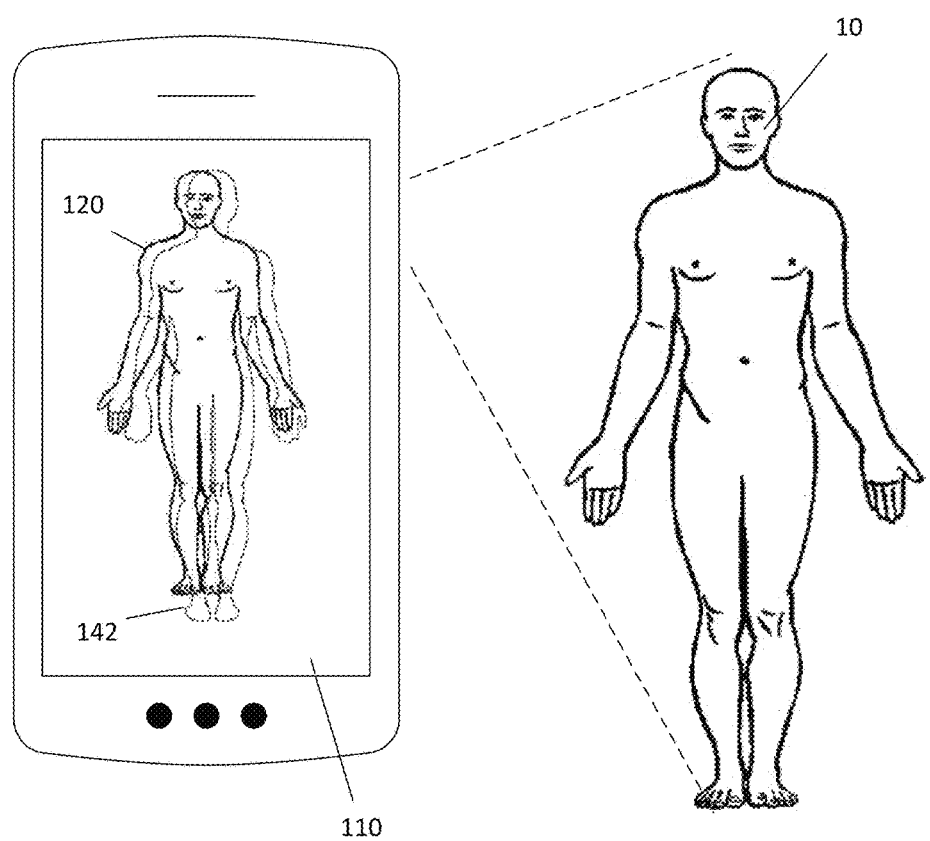
FIG. 5 is an illustration of the display of a computerized device utilizing the invention.

Referring to FIG. 5, on the display screen 110 of the client device 100, the system displays the video input 120 received by the camera. Over top of the video input 120 received by the camera the system displays a transparent guidance template 142. The transparent guidance 142 template displays the portion of the patient 10 which should be photographed by the patient 10. For instance, the template 142 may display an outline of a human head. The patient 10 is then directed to adjust the camera of the client device 100 so that the patient's head in the camera image matches the transparent guidance template 142 displayed on the display screen 110 of the client device 100. The patient 10 then takes a photograph of the patient's head. The image is then stored in the system as a baseline image for later comparison with additional images. The system may present any number of transparent guidance templates to the patient 10. In the preferred embodiment the system presents guidance templates covering every section of the patient's skin so that the patient 10 is directed to take photographs of the patient's entire body. The system then stores all images taken by the patient 10, linking the images with the position and part of the body photographed and template utilized.

Figure 6:
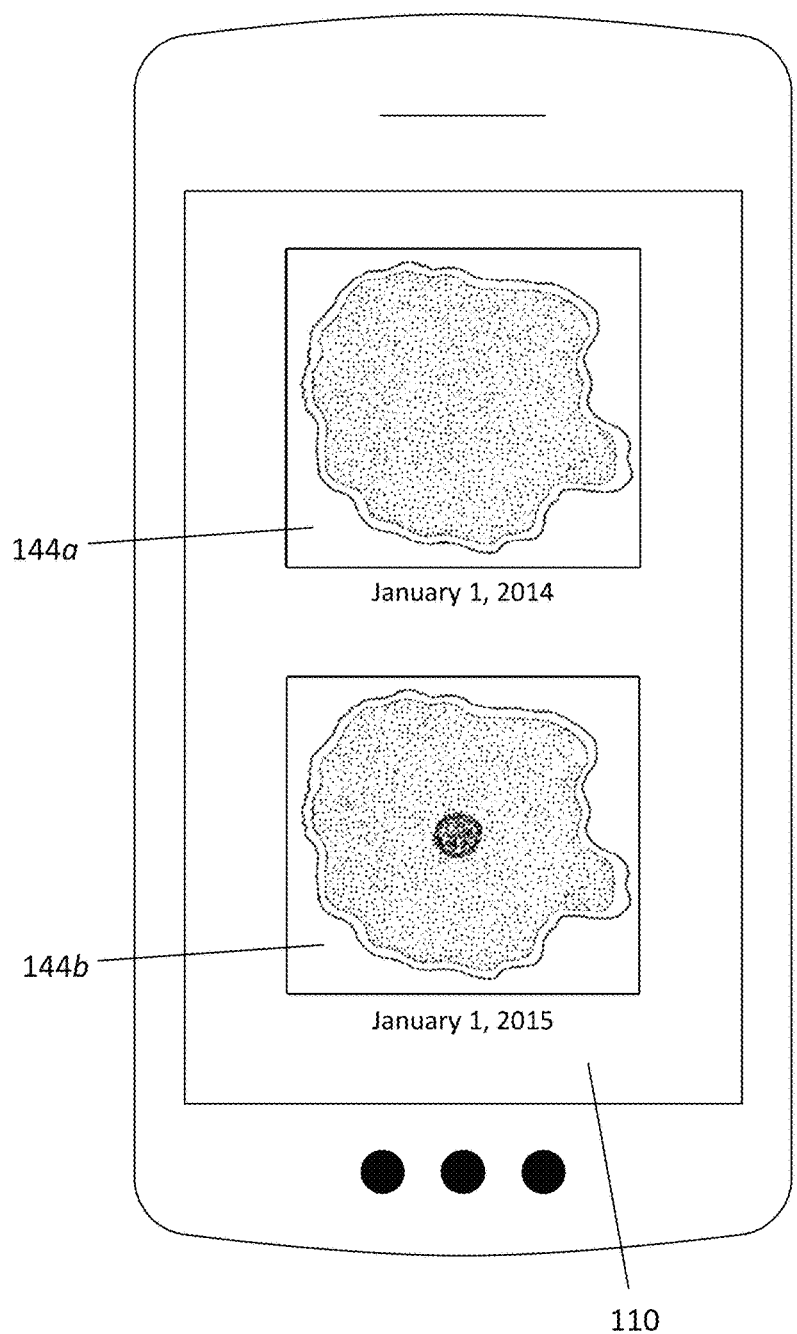
FIG. 6 is an illustration of the display of a computerized device utilizing the invention.

The system is configured to be repetitive in future cycles. In each iterance the patient 10 is directed to take photographs of the patient's body and detailed photographs of moles and skin lesions. The system tracks each series of photographs and information pertaining to each series of photographs. The information recorded may include date and time information of when the series of photographs were taken by the patient 10. When the patient 10 or physician reviews the images later taken, the system is configured to permit the patient 10 or physician to compare the images so that the patient 10 or physician may easily detect changes in the mole or lesion over time. The baseline images and subsequent images can be compared together in the system. The system also permits the patient 10 or physician to compare subsequent images to other subsequent images. For instance, if a patient 10 takes a series of baseline images on January 1, a series of subsequent images on June 1, and another series of subsequent images on December 1, the system permits the patient 10 to compare the images from December 1 against the images taken on June 1 or January 1. The system permits the patient 10 or physician to compare the images in any manner. Referring to FIG. 6, an example comparison of a first photographic image 144a and a second photographic image 144b is illustrated. In the example illustrated within FIG. 6, the first photographic image 144a is a first photograph capture of a dermatological lesion from Jan. 1, 2014 and the second photographic image 144b is a photograph capture of the same dermatological lesion from Jan. 1, 2015. The first photographic image 144a and second photographic image 144b are displayed side by side on the display screen 110 to allow easy comparison. By viewing together, as illustrated in the example, a user can see the appearance of a dark spot in the center of the dermatological lesion in the second photographic image 144b which was not seen in center of the dermatological lesion in the first photographic image 144a.

Figure 7:
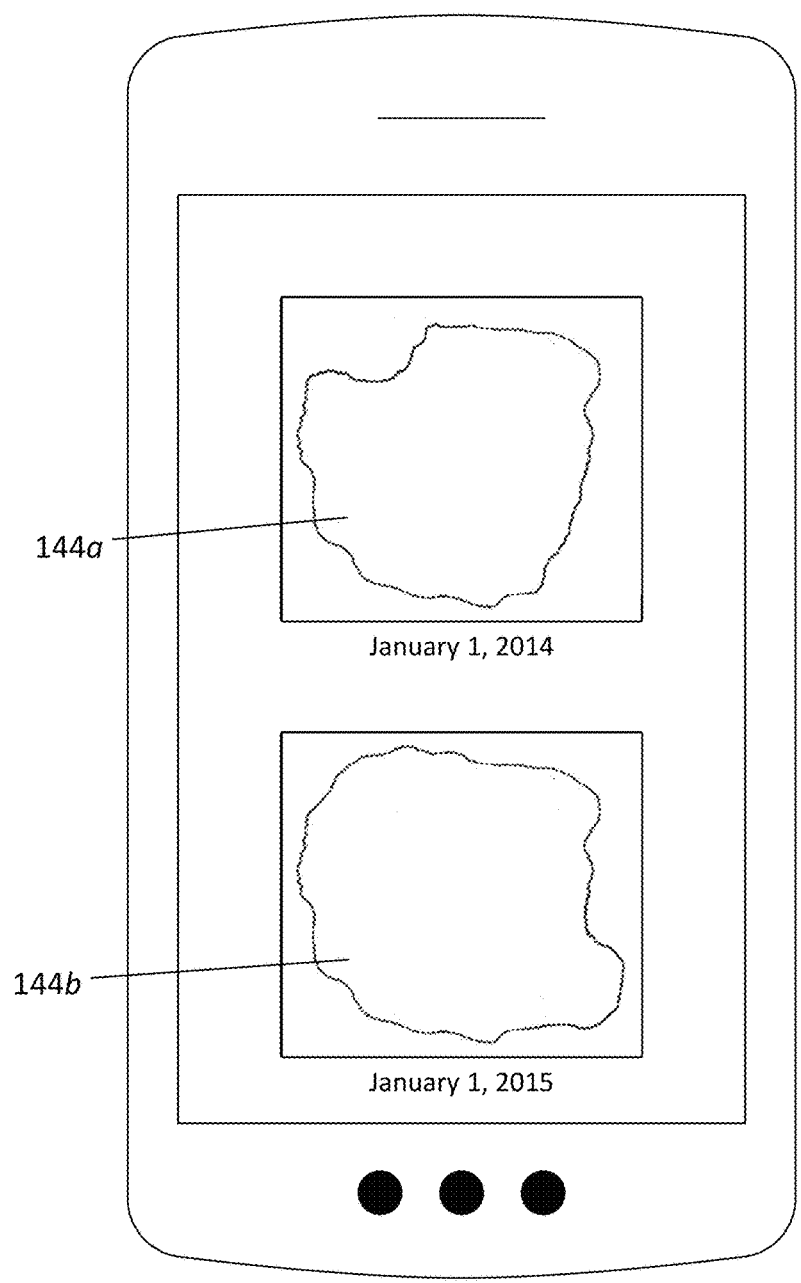
FIG. 7 is an illustration of the display of a computerized device utilizing the invention.
Figure 8:
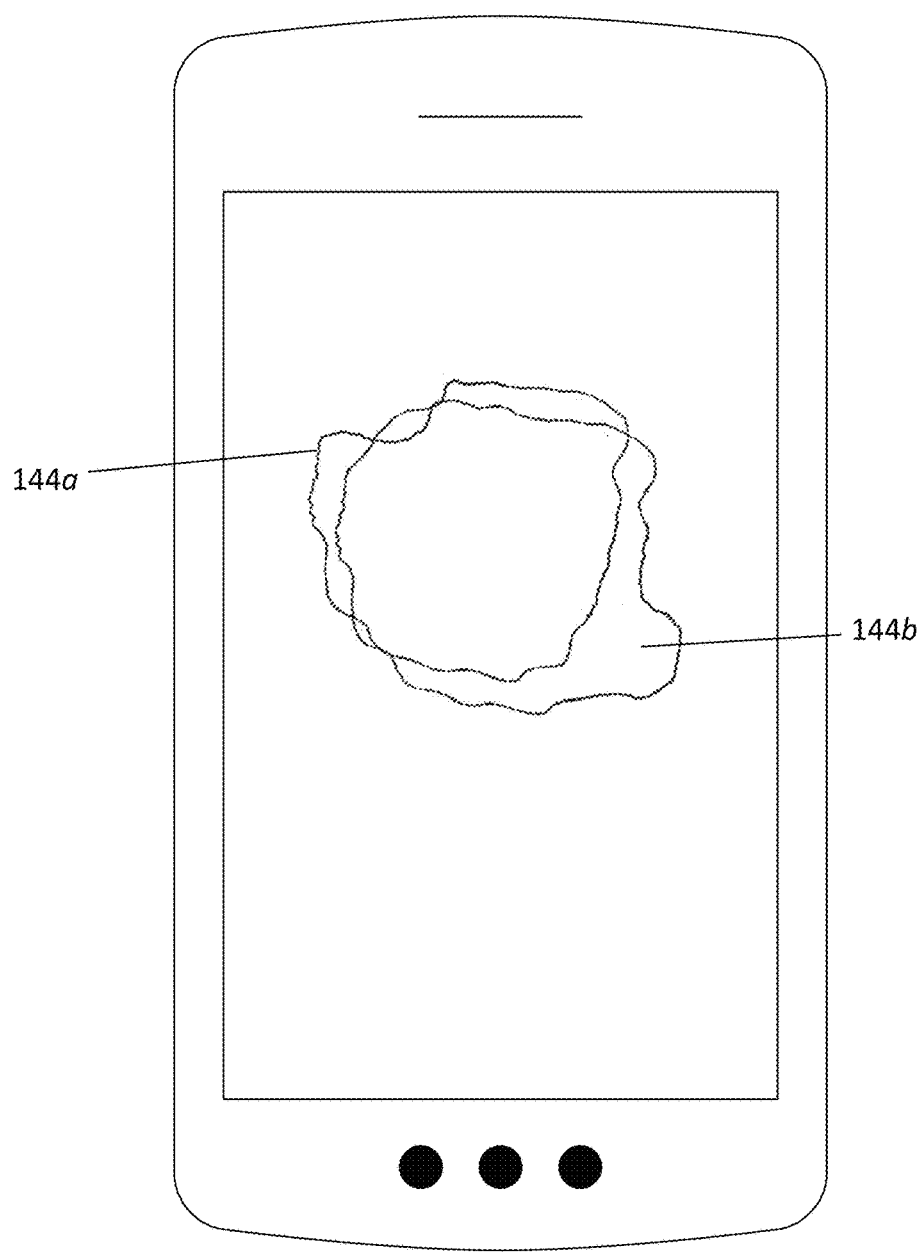
FIG. 8 is an illustration of the display of a computerized device utilizing the invention.
Figure 9:
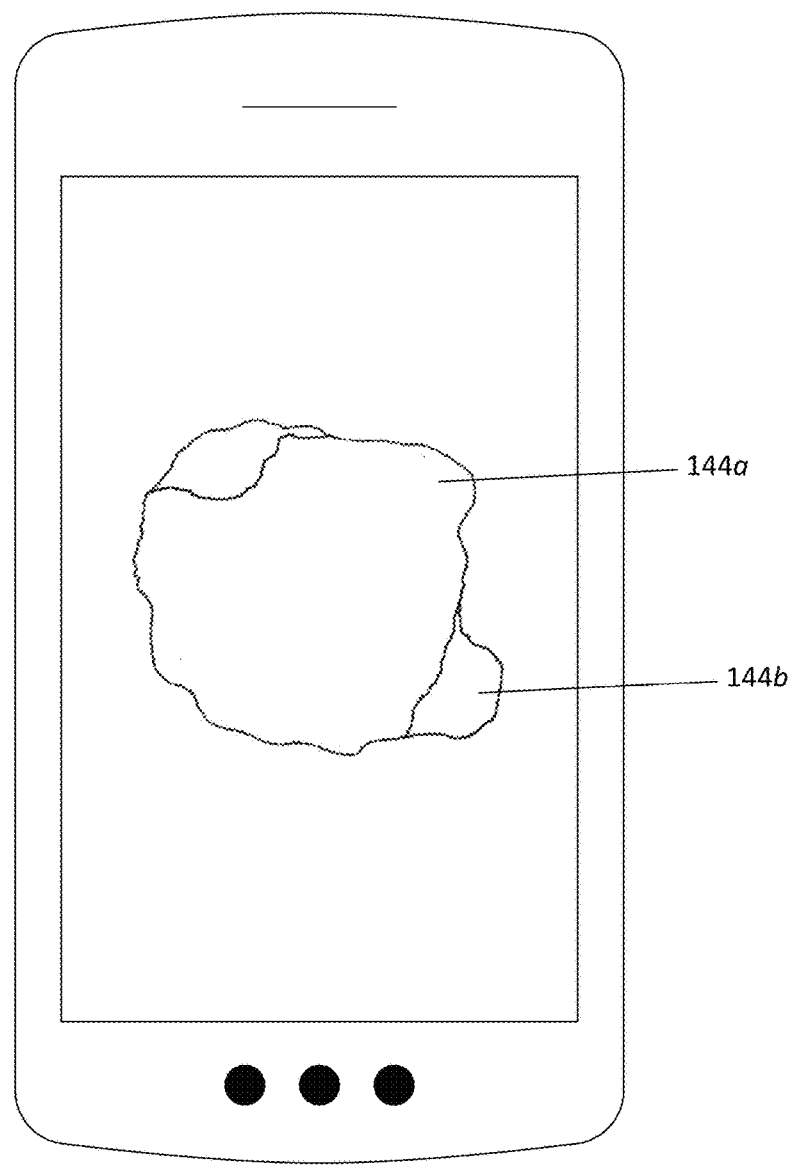
FIG. 9 is an illustration of the display of a computerized device utilizing the invention.
Figure 10:
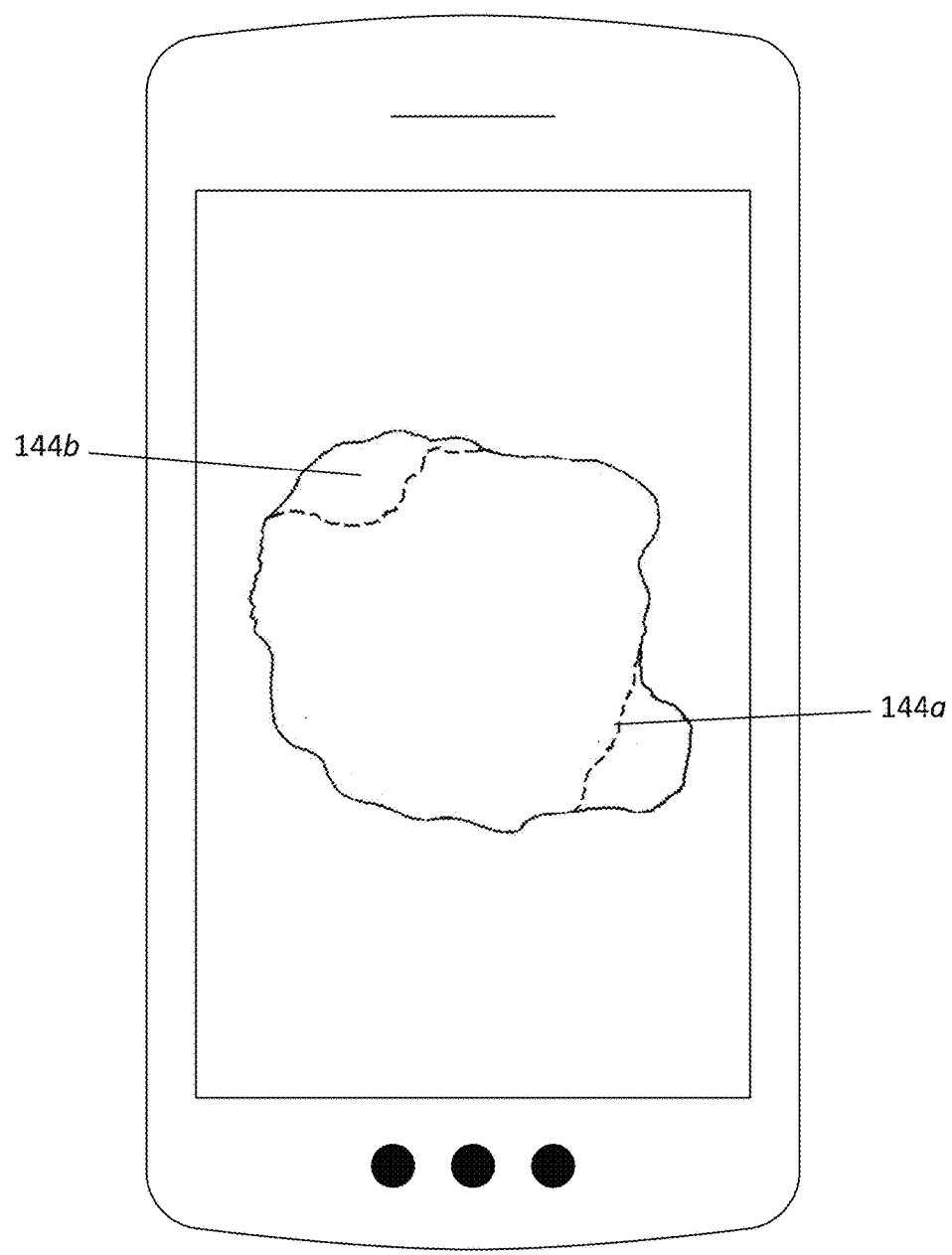
FIG. 10 is an illustration of the display of a computerized device utilizing the invention.

In the preferred embodiment the patient 10 may drag a subsequent image over a baseline image to create a composite image. In the composite image the subsequent image is transparent when overlaid on top of the baseline image so that features of the mole or lesion from each image can be matched together. The topographical features of the mole or lesion permit the patient 10 or physician to align the images of the mole or lesion. Any changes in color, size, or shape of the mole or lesion is readily apparent visually. In this manner the system permits the physician to easily make a diagnostic determination when viewing the images. The process of creating a composite image is illustrated by FIG. 7 through FIG. 10. As shown in FIG. 7, the first photographic image 144a is displayed adjacent to the second photographic image 144b. The user can touch the display screen 110 to drag either image over the other to create the composite image. As shown in FIG. 8, a user drags the second photographic image 144b over top of the first photographic image 144b to create the composite image. As shown in FIG. 9, the user aligns the topographical features of the lesions in the first photographic image 144a and the second photographic image 144b to create the composite image. In some instances the user may be required to enhance the zoom of either image to align the topographical features of the lesions so that the lesions are represented as the same size in the composite image. As shown by FIG. 10, the overlay of the first photographic image 144a and second photographic image 144b accents the changes in the dermatological lesion from Jan. 1, 2014 and Jan. 1, 2015. The accents can be created in any manner, such as by shading the portions of the images which are different, displaying the original image with a dotted line edge, presenting the differences between the two images in a specific predetermined color, or any other method which readily distinguishes the differences in the images visually. In this manner the system accents the changes in the dermatological features of the dermatological lesion over time.

Figure 11:
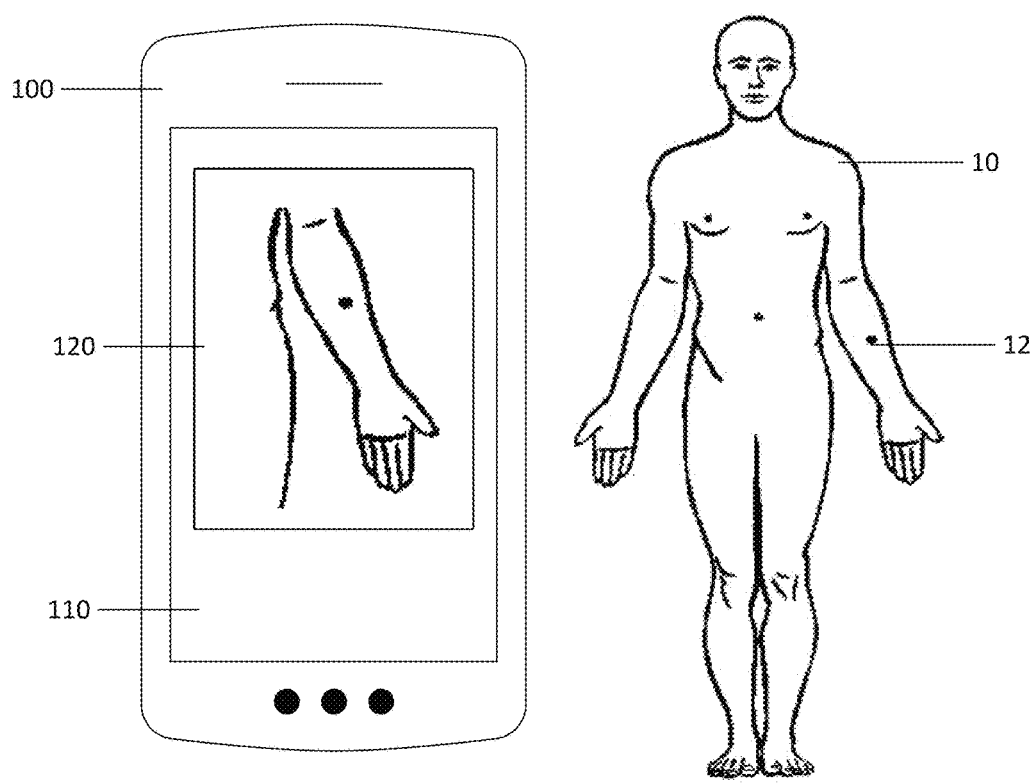
FIG. 11 is an illustration of the display of a computerized device utilizing the invention.
Figure 12:
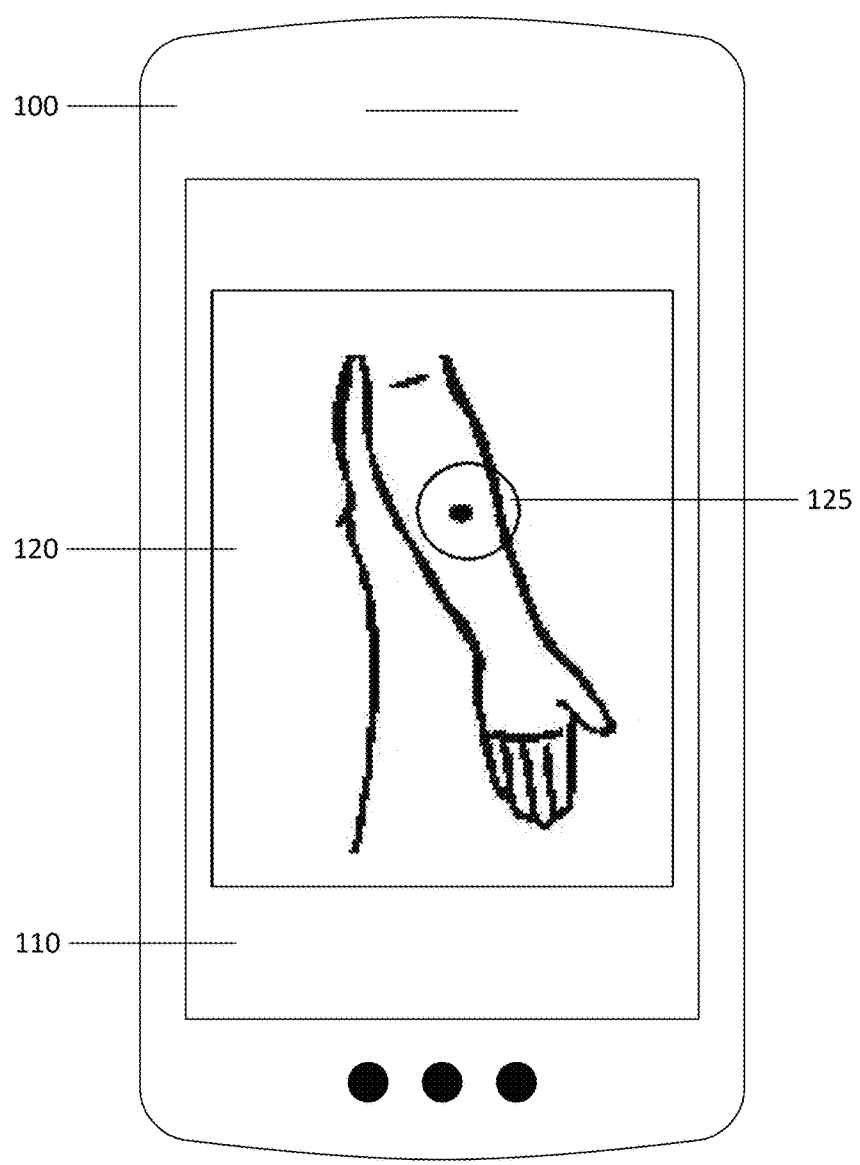
FIG. 12 is an illustration of the display of a computerized device utilizing the invention.
Figure 13:
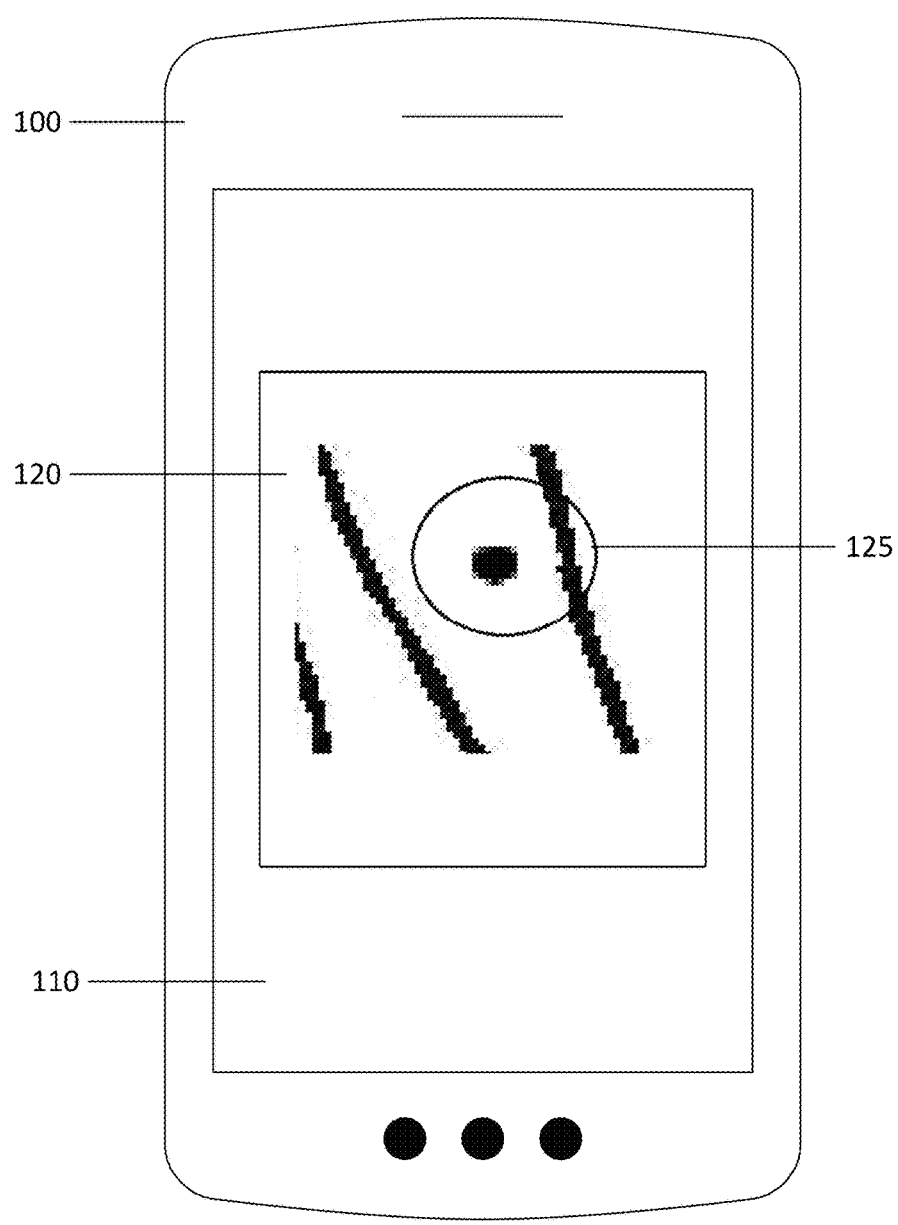
FIG. 13 is an illustration of the display of a computerized device utilizing the invention.

In an additional portion of the system, after the patient 10 has taken an initial photograph, the patient 10 may tag any moles or lesions viewable in the photograph. When the patient 10 tags the mole or lesion, the system presents the tagged mole or lesion in a highlighted fashion on the resulting image. The mole or lesion may be tagged in any fashion that draws visual distinction to the mole or lesion. The process of highlighting a mole or lesion is illustrated in FIG. 11 through FIG. 13. As shown in FIG. 11, the patient 10 has a mole 12 on the arm of the patient 10. The client device 100 is used to take a photograph of the patient 10. The display screen 110 displays a photograph captured from the video input 120. As shown in FIG. 12, once the patient 10 captures the image of the video input 120, the patient 10 can then create a highlight 125 over the image of the mole 12. In the preferred embodiment the tagged mole or lesion is represented within a red circle highlight 125.

After tagging a mole 12 or lesion with a highlight 125 the system seeks to have the patient 10 photograph the mole or lesion in detail, as shown in FIG. 13. When photographed in detail the mole or lesion should take up the majority of the image. The detailed photograph records the mole or lesion in sufficient detail to permit the patient 10 or physician to detect irregularities in the mole or lesion and to determine the size and shape of the mole or lesion. In some embodiments, the detailed photographs are taken by the patient 10 or physician with a dermatoscope 130. After taking the detailed photograph of the mole or lesion, the system stores the resulting images for later comparison. The system also stores information relating to the mole or lesion, such as location on the body and position of the mole or lesion in the image.

The system links the highlighting on the original image with the detailed image taken. When a patient 10 or physician later review the images in the system the patient 10 may click on the highlighted portion of the original image on the display screen 110. When the patient 10 clicks on the highlighted portion of the image the system presents the patient 10 with detailed image of the mole or lesion.

Figure 14:
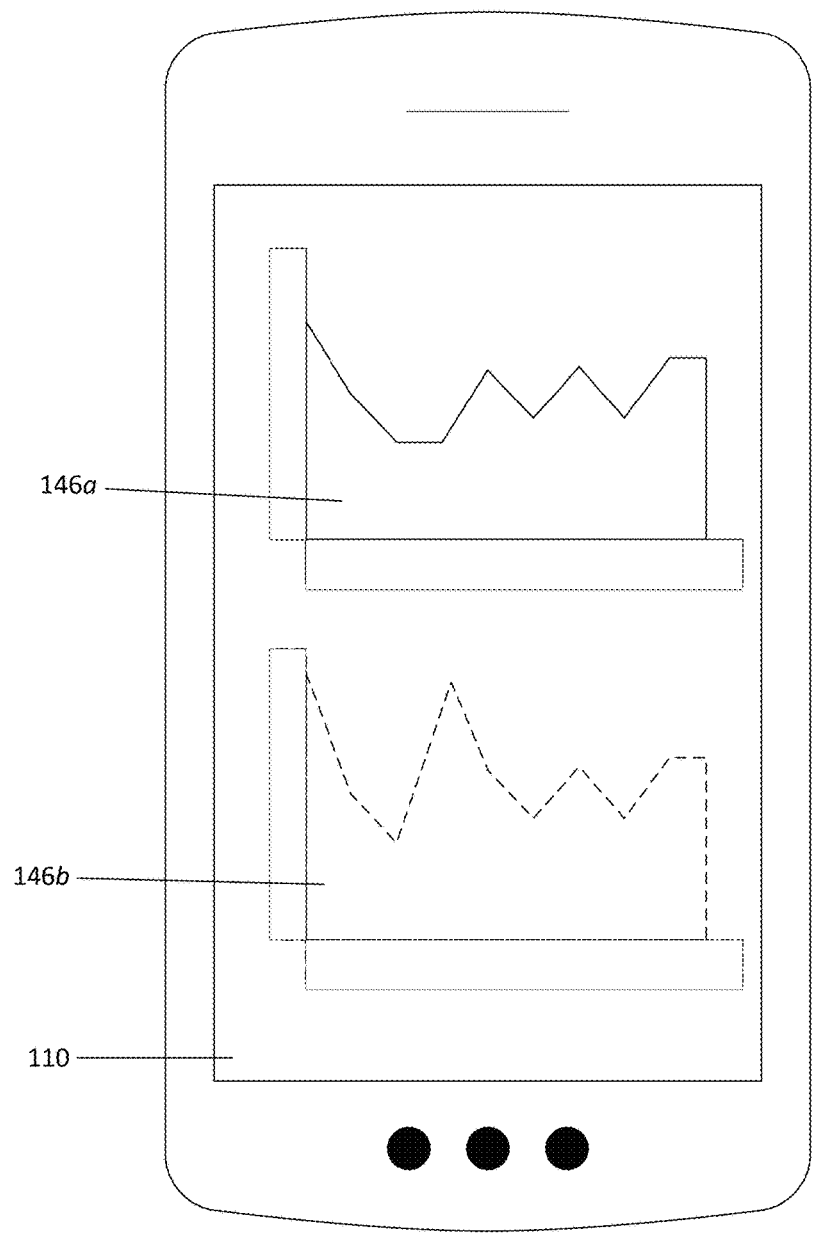
FIG. 14 is an illustration of the display of a computerized device utilizing the invention.
Figure 15:
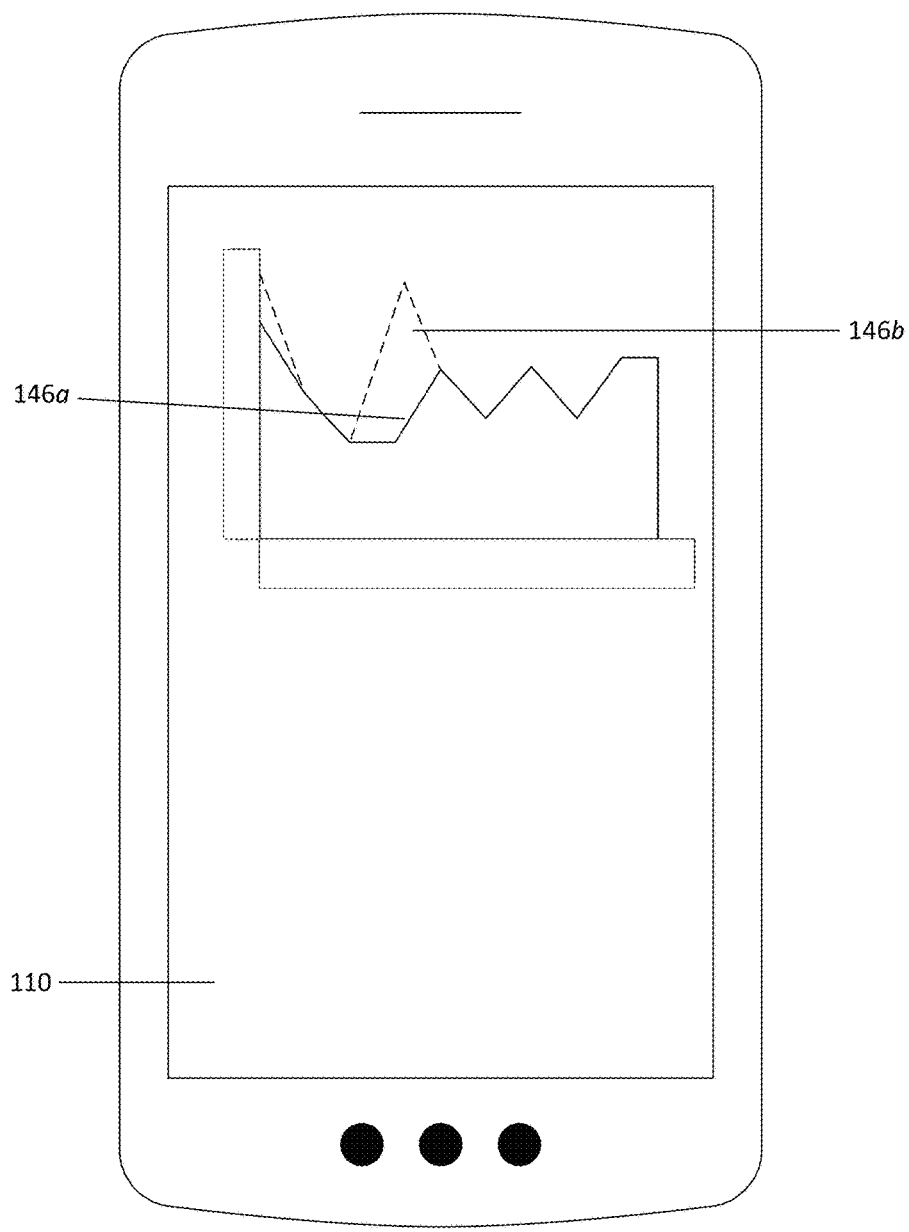
FIG. 15 is an illustration of the display of a computerized device utilizing the invention.

In another embodiment, the software may be used to track, record, and compare other, non-visual or physiological information about a patient 10. For instance, as illustrated in FIG. 14 and FIG. 15, the software may record the results of a patient's tests—such as blood tests or urine tests—or a patient's vital signs—such as pulmonary function, EKG reading, weight, or blood pressure. As shown in FIG. 14, the system displays a first set of test results 146a and a second set of test results 146b on the display screen 110. The results may be reviewed by viewing the results of a specific test on a specific date or by viewing a graph of the accumulative results as they change over time. In addition, as displayed in FIG. 15, the results of the first set of test results 146a and a second set of test results 146b may be directly compared by viewing the results overlapping as a merged image. For instance, the physician may view two EKG readings side by side, as in FIG. 14, or drag and overlay the two EKG readings to be able to directly compare the two visually, as in FIG. 15. In addition, any reports or readouts may be paired with related visual images. For instance an x-ray image may be paired with a written report from the physician interpreting the results.

Figure 16:
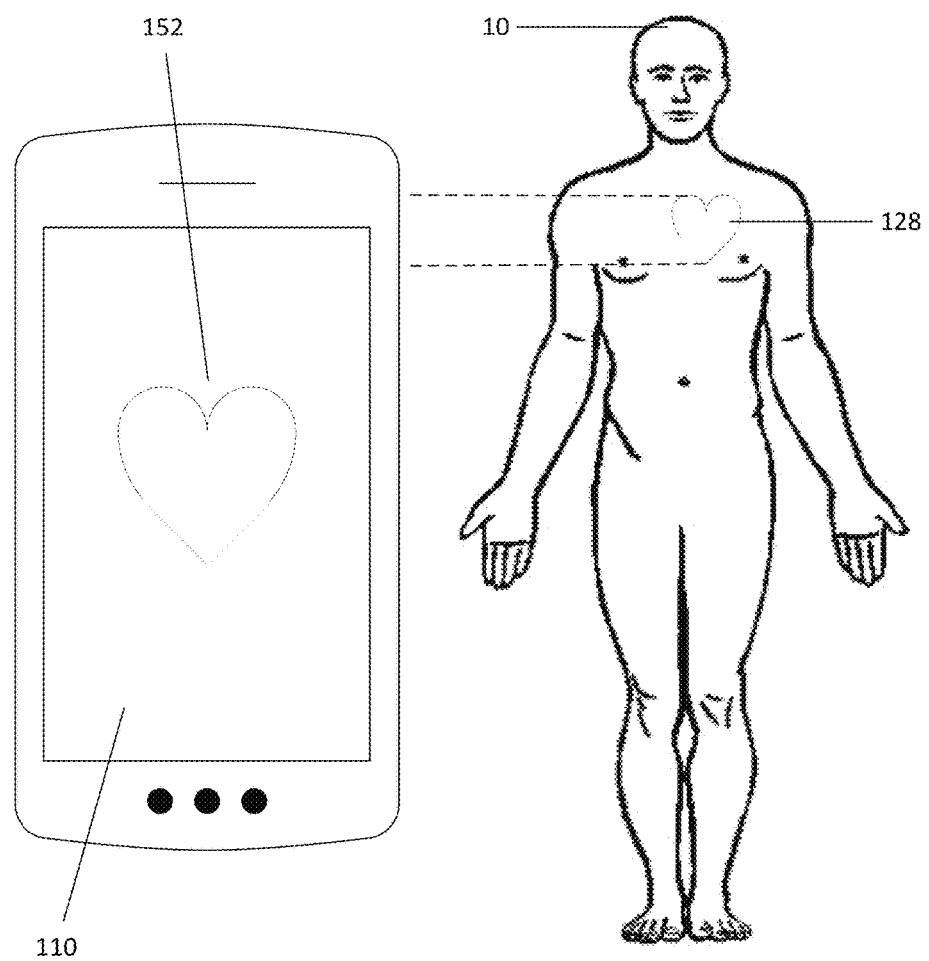
FIG. 16 is an illustration of the display of a computerized device utilizing the invention.

In another embodiment of the invention, the software has additional functionality particular to the needs of the physician, technician, or clinician. For instance, as illustrated in FIG. 16, the software may provide an organ template 152 on the display screen 110 for the photography and alignment of internal organs 128 and internal features for MRIs, x-rays, CAT scans, ultrasounds, radiation therapy, or any other type of internal reading or treatment. In the preferred embodiment, the system provides organ templates 152 of internal organs 128 for internal recording or treatment. For instance, the software may provide a template of a liver to a technician to take an ultrasound reading. The ultrasound readings are then recorded. At a later point in time the technician may take a second ultrasound reading and compare the images side by side or overlapped. Additionally, the reports from prior tests may be stored on the client device 100 and reviewed with a touch of the finger by scrolling through the reports from prior tests.

Figure 17:
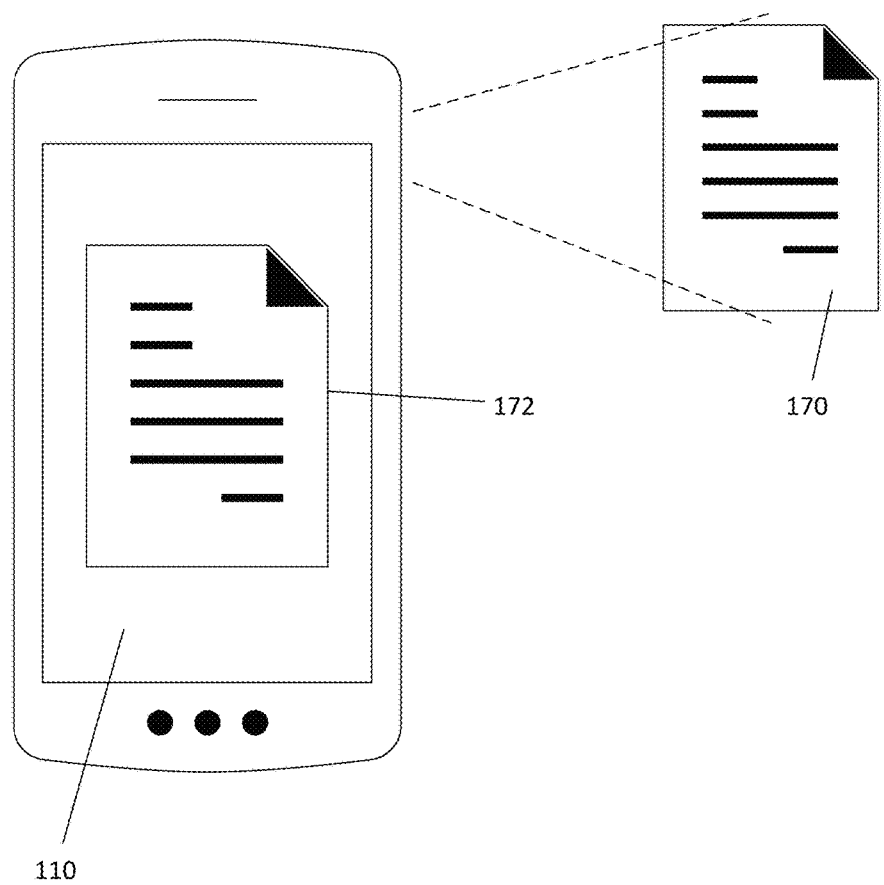
FIG. 17 is an illustration of the display of a computerized device utilizing the invention.

As illustrated in FIG. 17, the system also provides for a chart monitor component. The chart monitor component permits a patient 10 to take photographs of a medical chart 170 containing pathology reports and labs for the patient's record. The system permits storage of digital lab files 172 and health reports. The digital files 172 may be restricted solely to the patient 10 or may be shared between a patient 10 and the patient's physician. The patient 10 may review the digital files 172 at a later time when at a location remote from the physician's office. Alternatively, the patient 10 may review the digital files 172 with the physician in the physician's office. In some embodiments, a copy of the digital files 172 may be transferred and stored on the physician's device or on the server computer 132.

Figure 18:
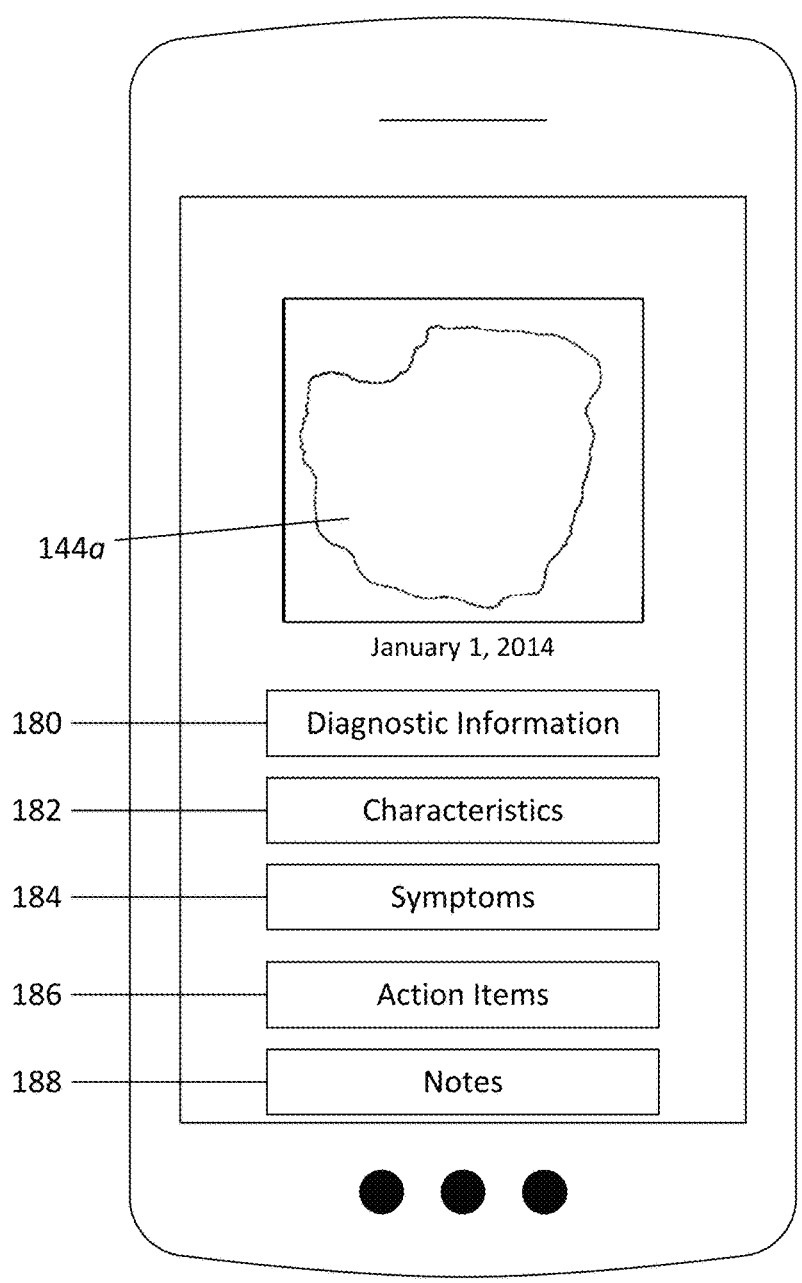
FIG. 18 is an illustration of the display of a computerized device utilizing the invention.

In another embodiment of the invention, the system utilizes an information input component which allows the patient 10 or the physician to enter relevant information about a mole or lesion into the system. The information entered into the system may be attached to a specific image of a specific mole or lesion. The information may be any information relevant about the mole or lesion or the treatment of such mole or lesion. As illustrated in FIG. 18, the first photographic image 144a of the lesion is displayed with a set of inputs about the dermatological lesion in the first photographic image 144a. The information may include the location and position of a mole or lesion, the diagnostic determination 180 of the mole or lesion by the physician, characteristics 182 about the mole or lesion, the symptoms 184 experienced by a patient 10 with regard to the mole or lesion, action items 186 for the physician or patient 10 to perform with respect to the mole or lesion, specific notes 188 about the mole of lesion, or any other relevant information. The diagnostic determination 180 can include any information about the diagnosis or prognosis of the lesion. The characteristics 182 can include any information about the size, shape, color, or other physical features of the lesion. The symptoms 184 can include any information about pain, irritation, or other experiences of the patient 10 with regard to the lesion. The action items 186 can include any specific actions that the physician may need to take with regard to the lesion (e.g. follow-up, test, biopsy, remove, medication, etc.). The information input system may include a series of radial dials or click boxes for the patient 10 or physician to click to record standard information about the mole or lesion. In the preferred embodiment the input component permits the recordation of freeform text.

In another embodiment of the system the software has a tracking component which ensures that the patient 10 tracks and takes photographs of the patient's skin in a timely and regular manner. The tracking component may be configured to track the times when a patient 10 should take photographs of the patient's skin. The tracking component may alert the patient 10 about the time when photographs should be taken. For instance, the system may be set up so that the patient 10 is scheduled to take photographs of the patient's skin every six months. When the six month time frame has elapsed the system may send a notification alert to the patient 10 that it is time to take photographs of the patient's skin. The system may remind the patient 10 in any manner, such as through email or text. The system may be configured to notify the patient 10 prior to the date on which the patient 10 is due to take the series of subsequent photographs or send a reminder after the date as a notification of a missing the session date for taking subsequent photographs.

In some embodiments the entire system, including the client device 100, may be restricted to a physician's office. In such a system the central server computer 132 would manage the system and the plurality of client devices 100 would be connected within the physician's office—such as in the separate patient 10 rooms. To avoid restrictions and regulations associated with government health agencies, the system does not autodiagnose any lesion or mole located on the patient's skin. The system is solely for the tracking and storage of information, all diagnosing is performed by the physician utilizing the system.

In another embodiment of the invention, the software further comprises an export/import feature. This feature permits a user to export information entered into a client device 100 to a separate device, system, server computer 132, or cloud storage. This feature permits the user to archive information about his or her profile at a specific date. The import feature permits the user to download information from a separate device, system, server computer 132, or cloud storage to a client device 100. The import feature permits the user to retrieve archived information about his or her profile. Additionally, the export/import feature may permit the user to transition his or her user profile from one client device 100 to a second client device 100.

The system may be used for other purposes than detailing and tracking skin lesions. The system may be used to track changes in any physical feature over time. For instance, the software may be used to track and compare images of wounds and wound status during the healing process. The software may be used to track and compare before and after images of cosmetic procedures. The software may be used to track any type of rash or other skin condition. In a broad sense, the software may be used by any person who wants to compare variations to his or her physical features. This may include a person who wants to compare different hair styles, different makeup, different clothes, different shoes, or completely different outfits.

The software may be used to record and store other information regarding treatment given by a physician, technician, or clinician. For instance, the software may monitor and track a patient's x-ray exposure through what x-rays, CAT scans, mammograms, or other procedures that a client has received. The system may track all procedures performed on a patient 10, including procedures involving radiation. The system may record the amount of radiation received by a patient 10 during a specific procedure as well as the total dosage received by a patient 10 over an extended period of time.

The software may be used to track a patient's medication. The software can track and present a report regarding each individual medication taken, the date each medication was started, how long each medication was taken, the dosage of each, the accumulated dosage taken over a certain period of time, and the frequency a patient 10 is to take the medication. In addition, the software may provide information, or hyperlinks to information, about the side effects of each medication and the interactions of multiple medications.

The software may be set up to retrieve information from other sources or components attached to the client device 100. The information may be in any format, such as a digital picture, pdf, spreadsheet, document, or other digital file.

In another embodiment, the software is configured to interface with a telemedicine application and the management of Electronic Medical Records (EMRs). In this embodiment the patient's records and photographs on the client device 100 may be sent seamlessly to a server computer 132 for the physician to review at a remote location.

The physician or clinician can review the patient's records and photographs prior to meeting with the patient 10 or in lieu of meeting with a patient 10. The physician or clinician may then make comments or recommendations for the patient 10 which are then transferred to the patient's client device 100.

Figure 19:
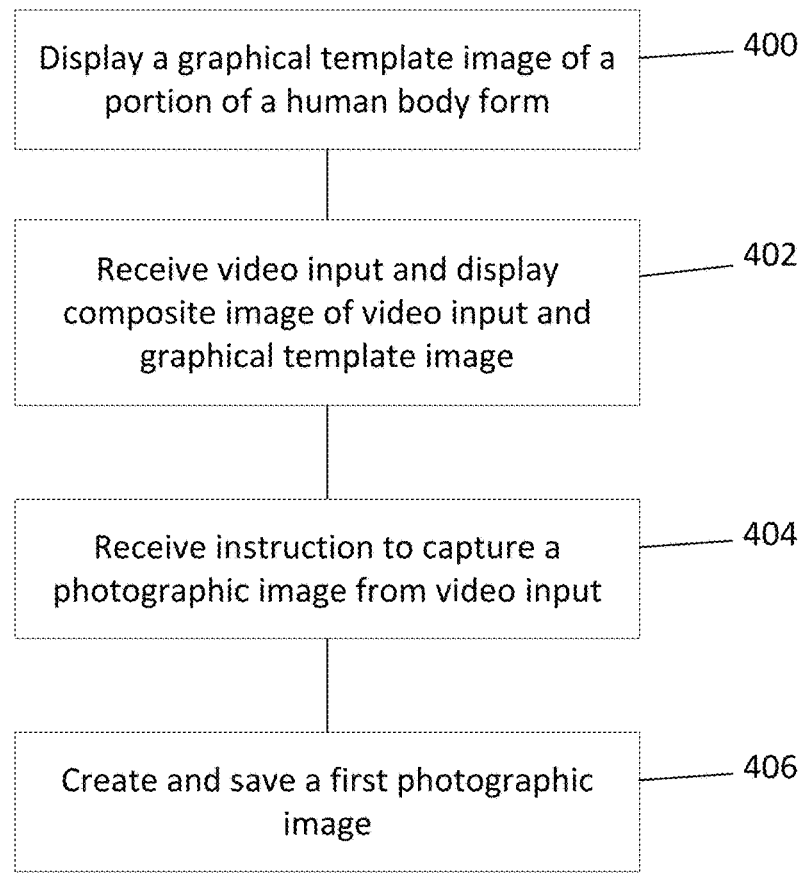
FIG. 19 is schematic of the inventive method performed by the system.

The inventive process of displaying a graphical template guidance is illustrated in FIG. 19. First the system displays a graphical template image of a portion of a human body form 400. Next the system receives a video input and displays a composite image of the video input and graphical template image 402. The system then receives an instruction to capture a photographic image from the video input 404. The system then creates and saves a first photographic image 406.

Figure 20:
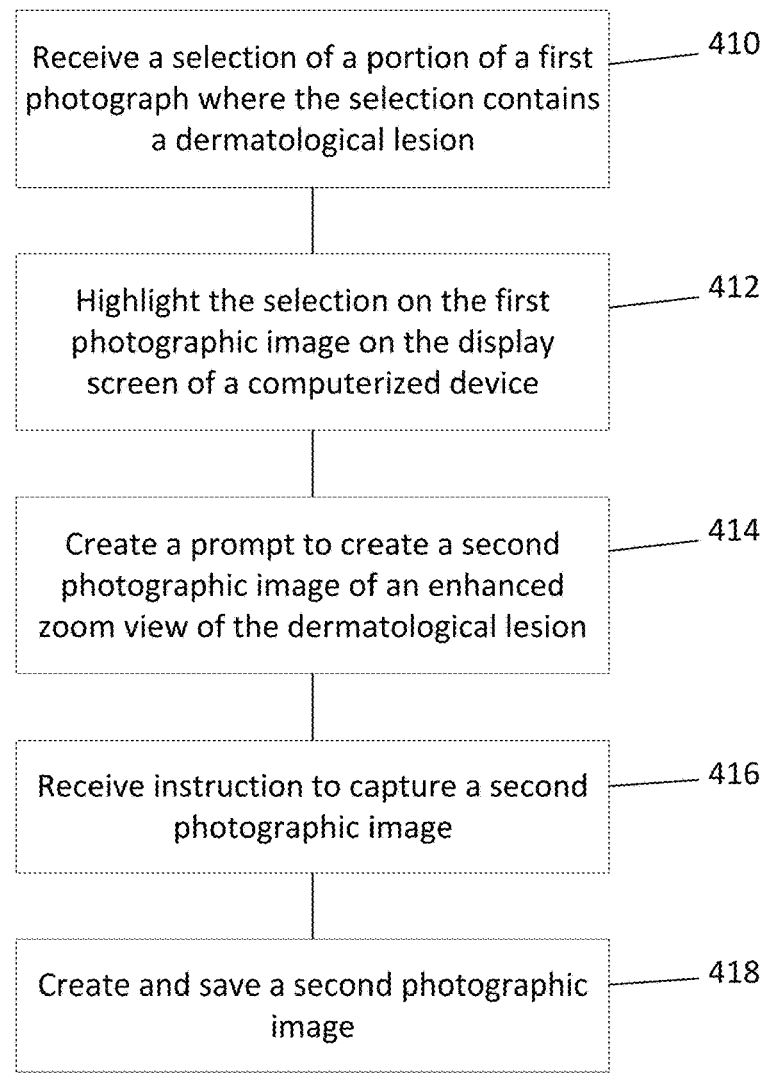
FIG. 20 is schematic of the inventive method performed by the system.

The inventive process of highlighting a dermatological lesion in the system is illustrated in FIG. 20. First the system receives a selection of a portion of a first photograph where the selection contains a dermatological lesion 410. The system then highlights the selection on the first photographic image on the display screen of the computerized device 412. The system creates a prompt to create a second photographic image of an enhanced zoom view of the dermatological lesion 414. The system receives an instruction to capture a second photographic image 416. The system then creates and saves a second photographic image 418.

Figure 21:
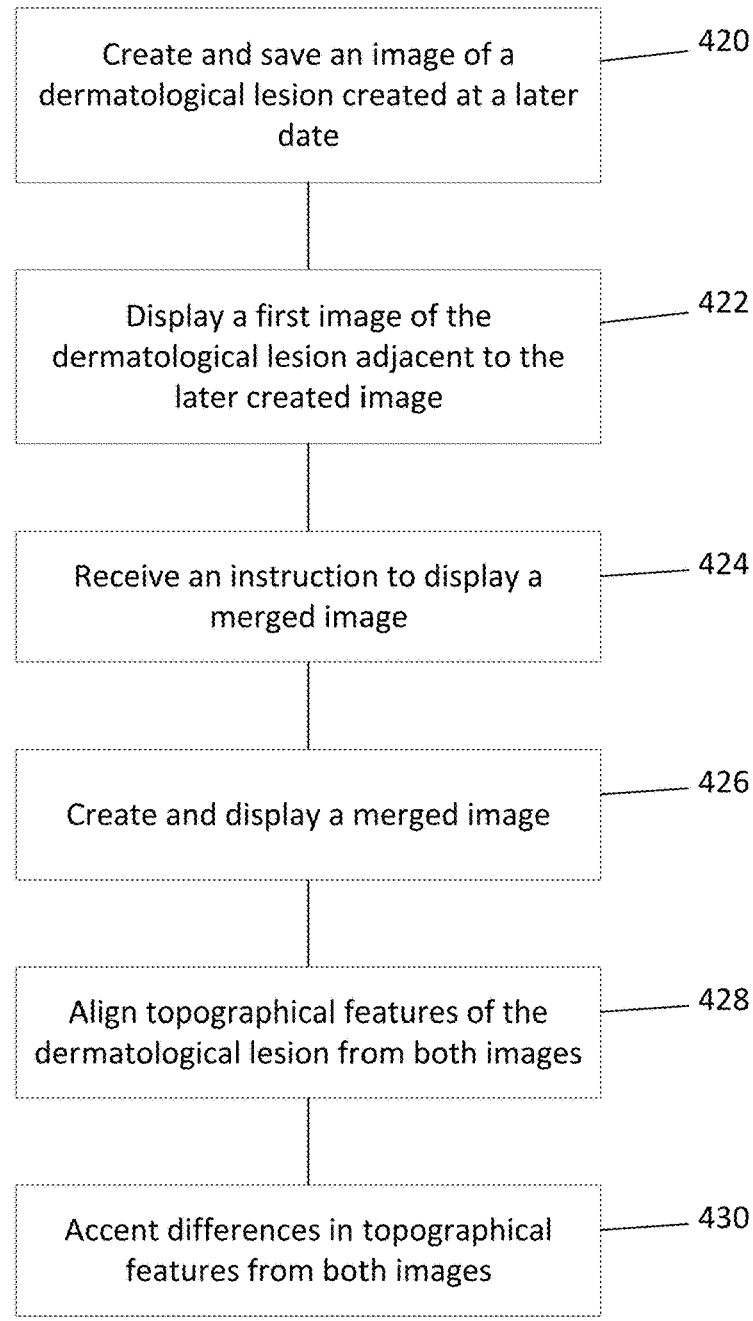
FIG. 21 is schematic of the inventive method performed by the system.

The inventive process of merging two images together to compare differences in a dermatological lesion is displayed in FIG. 21. After creating a baseline image, the system creates and saves a second image of the dermatological lesion created at a later date 420. The system then displays the baseline image of the dermatological lesion adjacent to the second image of the dermatological lesion 422. The system then receives an instruction to display a merged image of the two images 424. The system then creates and displays the merged image 426. The system aligns the topographical features of the dermatological lesion from both images 428. The system then accents the differences in topographical features of the dermatological features from both images 430.

What has been described above includes examples of the claimed subject matter. It is, of course, not possible to describe every conceivable combination of components or methodologies for purposes of describing the claimed subject matter, but one of ordinary skill in the art can recognize that many further combinations and permutations of such matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module, which may reside on a tangible, non-transitory computer-readable storage medium. Tangible, non-transitory computer-readable storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a tangible, non-transitory machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

The invention claimed is:

1. A computerized method for tracking and analyzing skin lesions comprising
   a) displaying a graphical template image on a display screen of a computerized device
      i) wherein said graphical template image consists of a portion of a human body form;
   b) receiving a video input from a camera;
   c) displaying said video input on said display screen;
   d) creating a composite image consisting of said graphical template image and said video input;
   e) displaying said composite image on said display screen;
   f) receiving an instruction to capture a photographic image from said video input;
   g) creating and storing a first photographic image from said video input;
   h) receiving a selection of a portion of said first photographic image, wherein said selection contains a dermatological lesion;
   i) highlighting said selection on said first photographic image on said display;
   j) creating a prompt to create a second photographic image in response to receiving a selection of a portion of said first photographic image, wherein said second photographic image is a zoomed image of said dermatological lesion;
   k) receiving an instruction to capture a second photographic image from said video input;
   l) creating and storing a second photographic image from said video input;
   m) creating and storing a third photographic image from said video input, wherein said third photographic image is a zoomed image of said dermatological lesion;
   n) displaying said second photographic image and said third photographic image adjacent on said display screen;
   o) receiving an instruction to display a merged image of said second photographic image and said third photographic image;
   p) creating a merged image of said second photographic image and said third photographic image;
   q) aligning one or more topographical features of said dermatological lesion in said second photographic image with one or more topographical features of said dermatological lesion in said third photographic image;
   r) accenting one or more differences in one or more topographical features between said dermatological lesion in said second photographic image and said dermatological lesion in said third photographic image to provide a physician with information to make a diagnostic determination with respect to the dermatological lesion.

2. The method as in claim 1 further comprising creating a red circle surrounding a selection on said first photographic image on said display.

3. The method as in claim 1 further comprising receiving a video input from a dermatoscope communicatively coupled to said computerized device.

4. The method as in claim 1 further comprising adjusting the transparency said second photographic image when creating said merged image.

5. The method as in claim 1 further comprising adjusting the transparency of said third photographic image when creating said merged image.

6. The method as in claim 4 further comprising adjusting the transparency of said third photographic image when creating said merged image.

7. The method as in claim 1 further comprising adjusting the transparency of said video input when creating said composite image.

8. The method as in claim 1 further comprising adjusting the transparency of said graphical template image when creating said composite image.

9. The method as in claim 1 further comprising
   a) requesting input regarding diagnostic information, one or more characteristics, one or more symptoms, and one or more action items of one or more dermatological lesions;
   b) receiving input regarding diagnostic information, one or more characteristics, one or more symptoms, and one or more action items of one or more dermatological lesions;
   c) storing input regarding diagnostic information, one or more characteristics, one or more symptoms, and one or more action items of one or more dermatological lesions;
   d) linking input regarding diagnostic information, one or more characteristics, one or more symptoms, and one or more action items of one or more dermatological lesions with a respective photographic image of a dermatological lesion;
   e) displaying input regarding diagnostic information, one or more characteristics, one or more symptoms, and one or more action items of one or more dermatological lesions adjacent to a respectively linked photographic image of a dermatological lesion.

10. The method as in claim 1 further comprising
    a) displaying an internal organ graphical template image on a display screen of a computerized device
       i) wherein said internal organ graphical template image consists of a portion of a human internal organ;
    b) receiving a video input from an internal imaging device coupled to said computerized device;
    c) displaying said video input from said internal imaging device on said display screen;
    d) creating an internal composite image consisting of said internal organ graphical template image and said video input from said internal imaging device;
    e) displaying said internal composite image on said display screen;
    f) receiving an instruction to capture a photographic image from said video input from said internal imaging device;
    g) creating and storing a first photographic image from said video input from said internal imaging device.

11. The method as in claim 1 further comprising
    a) creating a first test result image from a medical device input;
    b) creating a second test result image from a medical device input;
    c) displaying said first test result image and said second test result image adjacent on said display screen;
    d) receiving an instruction to display a merged test result image of said first test result image and said second test result image;

e) creating a merged image of said first test result image and said second test result image;
f) aligning one or more features of said first test result image with one or more features of said second test result image;
g) accenting one or more differences in one or more features between said first test result image and said second test result image.

12. The method as in claim 1 further comprising
a) receiving an instruction to create a password protected user ID;
b) creating a password protected user ID;
c) linking one or more photographic images to said password protected user ID;
d) receiving a request for access to one or more photographic images linked to said password protected user ID;
e) verifying the authenticity of a password associated with said password protected user ID;
f) displaying one or more photographic images on said display screen when said password is authenticated.

13. The method as in claim 1 further comprising
a) receiving a photographic image of a portion of a medical chart on said computerized device;
b) creating and storing a digital copy of said medical chart on said computerized device;
c) displaying said digital copy of said medical chart on said display screen.

14. A computerized method for tracking and analyzing skin lesions comprising
a) displaying a graphical template image on a display screen of a computerized device
i) wherein said graphical template image consists of a portion of a human body form;
b) receiving a video input from a camera;
c) displaying said video input on said display screen;
d) creating a composite image consisting of said graphical template image and said video input;
e) displaying said composite image on said display screen;
f) receiving an instruction to capture a photographic image from said video input;
g) creating and storing a first photographic image from said video input;
h) receiving a selection of a portion of said first photographic image, wherein said selection contains a dermatological lesion; and
i) highlighting said selection on said first photographic image on said display to provide a physician with information to make a diagnostic determination with respect to the dermatological lesion.

15. The method as in claim 14 further comprising
a) creating a prompt to create a second photographic image in response to receiving a selection of a portion of said first photographic image, wherein said second photographic image is a zoomed image of said dermatological lesion;
b) receiving an instruction to capture a second photographic image from said video input;
c) creating and storing a second photographic image from said video input.

16. The method as in claim 15 further comprising
a) requesting input regarding diagnostic information, one or more characteristics, one or more symptoms, and one or more action items of one or more dermatological lesions;
b) receiving input regarding diagnostic information, one or more characteristics, one or more symptoms, and one or more action items of one or more dermatological lesions;
c) storing input regarding diagnostic information, one or more characteristics, one or more symptoms, and one or more action items of one or more dermatological lesions;
d) linking input regarding diagnostic information, one or more characteristics, one or more symptoms, and one or more action items of one or more dermatological lesions with a respective photographic image of a dermatological lesion;
e) displaying input regarding diagnostic information, one or more characteristics, one or more symptoms, and one or more action items of one or more dermatological lesions adjacent to a respectively linked photographic image of a dermatological lesion.

17. A computerized method for tracking and analyzing skin lesions comprising
a) displaying a graphical template image on a display screen of a computerized device
i) wherein said graphical template image consists of a portion of a human body form;
b) receiving a video input from a camera;
c) displaying said video input on said display screen;
d) creating a composite image consisting of said graphical template image and said video input;
e) displaying said composite image on said display screen;
f) receiving an instruction to capture a photographic image from said video input;
g) creating and storing a first photographic image from said video input;
h) creating and storing a second photographic image from said video input, wherein said second photographic image is a zoomed image of said dermatological lesion;
i) displaying said first photographic image and said second photographic image adjacent on said display screen;
j) receiving an instruction to display a merged image of said first photographic image and said second photographic image; and
k) creating a merged image of said first photographic image and said second photographic image to provide a physician with information to make a diagnostic determination with respect to the dermatological lesion.

18. The method as in claim 17 further comprising
a) aligning one or more topographical features of a dermatological lesion in said first photographic image with one or more topographical features of a dermatological lesion in said second photographic image.

19. The method as in claim 18 further comprising
a) accenting one or more differences in one or more topographical features between said dermatological lesion in said first photographic image and said dermatological lesion in said second photographic image.

20. The method as in claim 19 further comprising
a) requesting input regarding diagnostic information, one or more characteristics, one or more symptoms, and one or more action items of one or more dermatological lesions;
b) receiving input regarding diagnostic information, one or more characteristics, one or more symptoms, and one or more action items of one or more dermatological lesions;

c) storing input regarding diagnostic information, one or more characteristics, one or more symptoms, and one or more action items of one or more dermatological lesions;

d) linking input regarding diagnostic information, one or more characteristics, one or more symptoms, and one or more action items of one or more dermatological lesions with a respective photographic image of a dermatological lesion;

e) displaying input regarding diagnostic information, one or more characteristics, one or more symptoms, and one or more action items of one or more dermatological lesions adjacent to a respectively linked photographic image of a dermatological lesion.

\* \* \* \* \*